(12) United States Patent
Doat et al.

(10) Patent No.: US 8,231,884 B2
(45) Date of Patent: Jul. 31, 2012

(54) DIFFUSING PARTICLES BASED ON ORGANOGELLING XEROGEL FIBERS, METHOD FOR PREPARING SAME AND USE IN COSMETIC FORMULATIONS

(75) Inventors: Anne Doat, Toulouse (FR); Emile Perez, Colomiers (FR); Isabelle Rico-Lattes, Auzielle (FR); Pascal Bordat, Mervilla (FR)

(73) Assignees: Pierre Fabre Dermo-Cosmetique, Boulogne-Billancourt (FR); Universite Paul Sabatier Toulouse III, Toulouse (FR); Centre National de la Recherche Scientifique (CNRS), Paris (FR)

( * ) Notice: Subject to any disclaimer, the term of this patent is extended or adjusted under 35 U.S.C. 154(b) by 1034 days.

(21) Appl. No.: 11/992,659

(22) PCT Filed: Sep. 29, 2006

(86) PCT No.: PCT/EP2006/066892
§ 371 (c)(1), (2), (4) Date: Apr. 30, 2008

(87) PCT Pub. No.: WO2007/039561
PCT Pub. Date: Apr. 12, 2007

(65) Prior Publication Data
US 2008/0248071 A1 Oct. 9, 2008

(30) Foreign Application Priority Data
Sep. 30, 2005 (FR) ...................................... 05 10035

(51) Int. Cl.
*A61K 8/60* (2006.01)
*A61K 8/11* (2006.01)
*A61Q 19/00* (2006.01)

(52) U.S. Cl. ........................................ 424/401; 514/738
(58) Field of Classification Search ........................ None
See application file for complete search history.

(56) References Cited

U.S. PATENT DOCUMENTS

| | | | | |
|---|---|---|---|---|
| 5,024,831 | A * | 6/1991 | Kurisaki et al. | 424/69 |
| 5,286,755 | A | 2/1994 | Kauffmann et al. | |
| 6,187,842 | B1 * | 2/2001 | Kobayashi et al. | 524/58 |

FOREIGN PATENT DOCUMENTS

| EP | 0 531 224 A1 | 3/1993 |
|---|---|---|
| EP | 0 894 492 A2 | 2/1999 |
| FR | 2 840 807 A1 | 12/2003 |
| WO | WO-03/105788 A2 | 12/2003 |
| WO | WO 03/105788 A2 | 12/2003 |
| WO | WO-2005/070382 A1 | 8/2005 |

OTHER PUBLICATIONS

Thierry et al. (Macromol. Symp. 2006, 241, 103-110).*
Watase et al., J. Phys. Chem. B, 1999, vol. 103, pp. 2366-2373.
Yamasaki et al., Bull. Chem. Soc. Jpn., vol. 68, 1995, pp. 123-127.
Wilder et al., Recent Res Devel. Mat. Sci. vol. 3, 2002, pp. 93-115.
Bruls et al., Photochemistry and Photobiology, vol. 40, No. 2, 1984, pp. 231-242.
Abdallah et al., Adv. Mater., 2000, vol. 12, No. 17, Sep. 1, 2002, pp. 1237-1247.
Terech., Low-molecular weight organogelators, in specialist Surfactants, I.D. Robb(ed.), Blackie Academic and Professional, Glasgow, 1996, pp. 208-268.
Markovic N et al: "Physical organogels: mechanism and kinetics of evaporation of the solvents entrapped within network scaffolding" Thermochimica Acta, Elsevier Science Publishers, Amsterdam, NL, vol. 427, No. 1-2, Mar. 2005, pp. 207-219.
D. R. Trivedi et al: "Structure-Property Correlation of a New Family of Organogelators Based on Organic Salts and Their selective Gelation of Oil from OilANater Mixtures" Chemistry-A European Journal, vol. 10, Nov. 5, 2004, pp. 5311-5322.
N. Amanokura et al: "New sugar-based gelators bearing a p-nitrophenyl chromophore: remarkably large influence of a sugar structure on the gelatin ability" Journal of the Chemical Society, Perkin Transactions 2: Physical Organic Chemistry, 1998, pp. 2585-2591.
Murdan S et al: "Non-Ionic Surfactant Based Organogels Incorporating Niosomes" Sciences Techniques Et Pratiques Sip Pharma Pratiques, Paris, FR, vol. 6, No. 1, 1996, pp. 44-48.
Terech P. et al: "Low Molecular Mass Gelators of Organic Liquids and the Properties of Their Gels" Chemical Reviews, ACS, Washington, DC, US, vol. 97, 1997, pp. 3133-3159.

* cited by examiner

*Primary Examiner* — David J Blanchard
*Assistant Examiner* — Garen Gotfredson
(74) *Attorney, Agent, or Firm* — Birch, Stewart, Kolasch & Birch, LLP

(57) ABSTRACT

The invention concerns particles consisting essentially of fibers of an organogelling substance in the form of xerogel (dry gel), the fibers being essentially oriented in a common direction and randomly aligned around the longest fiber. The organogelling substance is preferably 1,3: 2,4-di-O-benzylidene-D-sorbitol. Said particles, which are in the form of spindles, have interesting optical properties; they have a total light transmittance higher than 0.80, with a diffuse transmittance higher than the specular transmittance. The invention also concerns a method for preparing said particles by solvent evaporation process, by solvent diffusion/evaporation process or by shearing process. The invention finally concerns active particles consisting of said particles whereon is immobilized a dermocosmetically active principle, a dermocosmetic composition comprising said particles or said active particles and a cosmetic treatment method which consists in applying on the skin said dermocosmetic composition.

10 Claims, No Drawings

DIFFUSING PARTICLES BASED ON ORGANOGELLING XEROGEL FIBERS, METHOD FOR PREPARING SAME AND USE IN COSMETIC FORMULATIONS

This application is the U.S. national phase under 35 U.S.C. §371 of PCT/EP2006/066892, filed Sep. 29, 2006. Priority is claimed under 35 U.S.C. §119 to French application 0510035, filed Sep. 30, 2005.

The invention relates to new particles constituted essentially of fibers of an organogelator. These particles, which are oblong, have beneficial iridescent properties, in particular soft-focus effect properties.

Make-up and foundation are used to improve the visual appearance of the skin. However, these cosmetic products often tend emphasize the presence of wrinkles and lines or other imperfections of the skin. This undesirable effect is related in particular to the fact that the make-up builds up inside the creases formed by the wrinkles. Traditional make-up products generally contain iron oxide-based pigments so as to reproduce the skin tone. Thus, when the make-up is applied, these pigments are spread over the skin and fill the wrinkles, which enhances the tonality of the latter, thereby making them much more visible.

The appearance of wrinkles and lines of the skin results from a group of optical phenomena (Bruls, W. Vander Leun, J., *Forward scattering properties of human epidermal layers, Photochem. Photobiol.* 1984, 40, p. 231-242). When light hits an object, a number of events may occur depending on the nature of said object. Thus, the light can be completely reflected in a direction according to the angle of incidence, just like a mirror. Another possibility is that the light is diffused in all directions in space; this is diffuse reflection. Also, the light can be transmitted through the object if the object is sufficiently transparent. This phenomenon can also involve refraction of the light. When the light passes through an object, its speed of propagation as well as its wavelength change according to the refractive index, which is defined as the ratio of the propagation speed of light in a vacuum over the propagation speed of light inside of the object. When light hits the surface of the skin, it is partially absorbed, reflected and diffused, but for a given observer, the visual appearance of the skin will depend in particular on the amount of light absorbed and diffused. Thus, when light hits a wrinkle, it cannot be diffused or even reflected, which will give it the appearance of a dark line. In this case, the light is trapped inside the crease of the wrinkle, just like the inorganic pigments. This is related to the fact that the light undergoes a plurality of reflections inside the wrinkle and cannot return to the observer. As a result of this trapping the eye perceives a decrease in the light at the level of the wrinkles, which makes them darker.

To attenuate the appearance of wrinkles and lines, make-up or foundation formulations can be modified by incorporating pigments capable of manipulating light and thus modifying the appearance of the surface to which they are applied. Numerous cosmetic products therefore use diffusing powders or particles so as to enhance the appearance of the skin. To mask skin wrinkles, the main function of the particles diffusing light is to prevent the light from being trapped inside the crease of a wrinkle or a line. A particle diffusing light can be, for example, titanium dioxide, which will physically fill the creases and reflect light. Thus, U.S. Pat. No. 6,174,533 describes topical compositions intended to improve the appearance of skin, which contain titanium oxide particles. However, with this type of reflective material, the wrinkle or line is not masked, but instead emphasized. The titanium dioxide particles have this undesirable effect because they are too opaque and reflective. Consequently, it is essential for this type of use that the material not only reflect light, but that it also have a certain degree of transparency so as to prevent the "mask" effect of titanium dioxide.

Certain cosmetic products use particles that create a soft-focus effect in order to mask wrinkles and make the skin brighter. Such particles have the property of diffusing light, which produces a natural satin effect, unlike opaque particles (such as $TiO_2$), which whiten the skin and give a matte appearance. To obtain a soft-focus effect, light diffusers must combine a certain number of properties. First, the amount of light absorbed must be minimal. The total transmission must be high, because transparent materials have a more natural appearance. The nature of the light transmitted must be primarily diffuse so that the lighting is uniformly distributed on the surface of the skin. The total reflection (specular reflection creating a mirror effect) should be minimized, because a glossy effect will emphasize the presence of wrinkles, so the diffuse component of this reflection must be high.

Various non-biodegradable particle materials, both organic and inorganic, can be used as light diffusers. The most commonly used inorganic materials are talc, titanium dioxide, boron nitride, mica, silica, alumina, bismuth oxychloride and barium sulfate. Also, particles constituted by organic materials such as polymers, nylon-6, nylon-12, silicons, polymethyl methacrylate (PMMA), polystyrene and PMMA/polystyrene copolymers are used. The particles are available in various forms: flat particles, flakes, spheres, needles, and have a size ranging from 1 to 50 microns and refractive indices of 1.45 to 2.50. Also, combinations of these various materials, as well as composites combining materials with different refractive indices, can be used. For example, flat talc particles or polystyrene beads coated with titanium dioxide or iron oxide.

Thus, the Japanese patent application JP 2004 067535 describes the use in make-up of transparent powder having a soft-focus effect, made up of a mixture of mica or sericite with a titanium mica. The Japanese patent application JP 2001 199839 also describes a soft-focus effect powder made up of silica and metal. The U.S. Pat. No. 6,432,535 claims fine flakes of pigment constituted by silica particles coated with titanium dioxide.

Those skilled in the art are searching for other particles capable of providing this soft-focus effect.

Surprisingly, the inventors have developed new particles based on organogelator fibers in xerogel form, which have beneficial iridescent properties. In particular, these properties have a soft-focus effect.

In the sense of this invention, the term "organogelator" refers to an organic molecule capable of gelling, in small proportions, a wide range of organic solvents (cf: Terech P. & al. *"Low molecular mass gelators of organic liquids and the properties of their gels"*, Chemical Reviews 1997, 97 (8), p. 3133-3159 or Abdallah D. J. & al. *"Organogels and low molecular mass organic gelators"* Advanced materials 2000, 12, (7), p. 1237-1243 or Terech P. *"Low molecular weight organogelators"* in Specialist Surfactants I.D. Robb (Ed), Blackie Academic and Professional, Glasgow. 1996, p. 208-268).

The organogelators derived from carbohydrates or polyols such as xylitol or sorbitol are described in the following publications:

Watase, M., Nakatani, Y., Itagaki, H., *On the origin of the formation and stability of physical gels of di-O-benzylidene-D-sorbitol. J. Phy. Chem. B.* 1999, 103: p. 2366-2373;

Yamasaki, S. Y., Tsusumi, H., *The dependence of the polarity of solvents on 1,3:2,4-Di-O-benzylidene-D-sorbitol gel*, Bull. Chem. Soc. Jpn, 1995, 68: p. 123-127; and Wilder, E. A., Hall, C. K., Khan, S. A., Spontak, R. J., *Molecular self-organization and gelation efficacy of dibenzylidene sorbitol: An overview*, Recent Res. Devel. Mat. Sci. 2001, 3: p. 93-115;

and the gels resulting therefrom are known for their use in deodorant sticks: U.S. Pat. No. 6,338,841 and U.S. Pat. No. 5,964,691. In the case of deodorant sticks, the gelling occurs in bulk without the presence of particles of any shape.

The invention relates to oblong particles in the form of a mass constituted essentially by a plurality of fibers of an organogelator in xerogel form, in which the fibers are essentially oriented according to the same main direction defining the length of the particle, which is between 2 and 100 μm.

In the context of the invention, the term organogel refers to the gel formed by the organogelator and the solvent or liquid (to which said organogelator is added). This organogel can be viscous, semi-solid or in the form of an immobilized liquid. Xerogel is the product obtained when the solvent contained in the organogel is evaporated. It is a dry gel with a matrix formed by fibers of the organogelator.

In the context of this invention, the fibers of the organogelator in xerogel form organize together to form particles. It is not necessary to add another component, in particular a polymer, to obtain these particles.

Thus, the use of the phrase "essentially constituted by a plurality of fibers of an organogelator in xerogel form" means that at least 80% (weight/weight (p/p)) of said mass is constituted by said fibers of an organogelator in xerogel form, advantageously at least 90% (p/p) of said mass is constituted by said fibers, and even ore advantageously at least 98% (p/p) of said mass is constituted by said fibers.

The particles comprise an external envelope, including a polymer or a surfactant, enveloping said fiber mass. The addition of an external envelope, including a surfactant or a polymer, makes it possible to stabilize the dispersion of the droplets formed by the fibers of the organogelator in xerogel form and also to protect the particles formed. The surfactant can be a cationic, anionic, nonionic or zwitterionic surfactant molecule. In particular, the surfactant can be polyoxyethylene sorbitan monooleate (Tween® 80). The polymer is advantageously a water-soluble polymer. The water-soluble polymer can advantageously be polyvinyl alcohol (PVA) hydrolyzed at 98-99%, with an average molecular weight Mw of between 5000 and 100,000 g·mole$^{-1}$, and preferably between 30,000 and 50,000 g·mole$^{-1}$.

The organogelator will advantageously be chosen from the group including substituted fatty acids as well as monovalent, divalent or trivalent metal salts thereof; steroid derivatives; polyaromatic derivatives; macrocycles; sugar derivatives; fluorinated or partially fluorinated compounds; fatty amines; alkanes; long-chain ammonium carbamates; cholesterol derivatives; amides; bis-ureas as well as all other possible combinations of these organogelators.

According to this invention, the organogelator will preferably be selected from carbohydrate or polyol derivatives such as xylitol or sorbitol.

In particular, the organogelator is the product of the condensation reaction between:
2 moles of an aldehyde of formula H—CO—R, with the radical R being chosen from the group constituted by:
single or fused aromatic radicals at $C_6$-$C_{14}$,
single or fused cycloalkyl radicals at $C_3$-$C_{14}$,
single or fused heterocyclic radicals at $C_2$-$C_{14}$,
saturated or unsaturated, linear or branched alkyl radicals at $C_1$-$C_{12}$,
aralkyls at $C_7$-$C_{20}$, in which the radical R can be substituted by one or more radicals chosen from the group constituted by the single or fused aromatic radicals at $C_6$-$C_{14}$, the single or fused cycloalkyl radicals at $C_3$-$C_{14}$, the single or fused heterocyclic radicals at $C_2$-$C_{14}$, the saturated or unsaturated, linear or branched alkyl radicals at $C_1$-$C_{12}$, or the halogen atoms, —$NH_2$, —OH, —$NO_2$, —CN, and —COOH; and
1 mole of a polyol of formula $HOCH_2(CHOH)_nCH_2OH$, in which n is 3, 4 or 5.

As examples of single aromatic radicals, the following can be cited: phenyl, tolyl, xylyl, mesityl, cumenyl and the like. As examples of fused aromatic radicals, the following can be cited: naphthyl, anthryl, phenanthryl and the like.

By the phrase "single or fused cycloalkyl at $C_3$-$C_{14}$", we mean a saturated carbocyclic ring with 3-14 chains, for example cyclopropyl, cyclobutyl, cyclopentyl, cyclohexyl and the like.

As used in this document, the phrase "single or fused heterocyclic radicals at $C_2$-$C_{14}$" refers to a heterocyclic ring with at least 3 chains, saturated or unsaturated, containing at least one heteroatom chosen from the group constituted by oxygen, nitrogen and sulfur. This heterocyclic ring can be fused to another heterocyclic ring or to a cyloalkyl or aromatic ring. As non-limiting examples of heterocyclic rings, the following can be cited: thienyl, pyrrolyl, imidazolyl, pyrazolyl, isothiazolyl, pyridyl, pyrazinyl, pyrimidinyl, pyridaznyl, pyrrolidinyl, pyrrolinyl, imidazolidinyl, pyrazolidinyl, pyrazolinyl, piperidyl, piperazinyl, furyl, pyranyl, isoxazolyl, morpholinyl, furazanyl, oxazolyl, oxazolidinyl, oxazolinyl, benzofuranyl, indolizinyl, indolyl, quinolyl, chromany and indolinyl.

The phrase "saturated or unsaturated alkyls" in the context of this invention refers to alkanes, alkenes or alkynes. In particular, the term "saturated alkyls" refers to alkyl radicals comprising 1 to 12 carbon atoms, and advantageously 1 to 6 carbon atoms, linear or branched. As examples of alkyl radicals comprising 1 to 6 carbon atoms, the following can be cited: methyl, ethyl, propyl, butyl, pentyl, hexyl, isopropyl, terbutyl. The term "unsaturated alkyls" refers to alkenyl radicals (at least one double bond), for example vinyl, allyl or the like, or alkynyl (at least one triple bond) comprising 2 to 12 carbon atoms, and advantageously 2 to 6 carbon atoms, linear or branched.

The term "aralkyl" in the context of this invention refers to preferably single aromatic radicals, bound to saturated alkyl radicals (as defined above), such as, for example, benzyl or phenethyl.

The term "halogen" refers to chlorine, fluorine, iodine and bromine.

In the sense of this invention, a polyol refers to an alcohol containing at least three hydroxyl radicals, each being bound to a different carbon atom. The polyol is advantageously an alcohol containing 5 or 6 hydroxyl radicals, preferably xylitol or sorbitol.

The organogelator advantageously has the following formula (I)

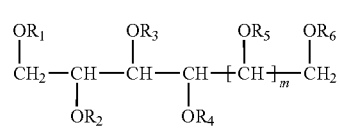

in which
m is 0 or 1
$R_1$ and $R_3$, $R_2$ and $R_4$, $R_5$ and $R_6$ represent a hydrogen atom or $R_1$ and $R_3$ and/or $R_2$ and $R_4$ and/or $R_5$ and $R_6$ together form a methylene radical substituted by a radical R chosen from the group constituted by:

single or fused aromatic radicals at $C_6$-$C_{14}$,
single or fused cycloalkyl radicals at $C_3$-$C_{14}$,
single or fused heterocyclic radicals at $C_2$-$C_{14}$,
saturated or unsaturated, linear or branched alkyl radicals at $C_1$-$C_{12}$,
aralkyls at $C_7$-$C_{20}$,
in which the radical R can be substituted by one or more radicals chosen from the group constituted by the single or fused aromatic radicals at $C_6$-$C_{14}$, the single or fused cycloalkyl radicals at $C_3$-$C_{14}$, the single or fused heterocyclic radicals at $C_2$-$C_{14}$, the saturated or unsaturated, linear or branched alkyl radicals at $C_1$-$C_{12}$, or the halogen atoms, —$NH_2$, —OH, —$NO_2$, —CN, and —COOH;

$R_1$, $R_2$, $R_3$, $R_4$, $R_5$ and $R_6$ do not all represent a hydrogen atom at the same time.

The radical R advantageously represents an unsubstituted phenyl radical or a phenyl radical substituted by 1 to 3 radicals chosen from the group including alkyl radicals at $C_1$-$C_4$, the halogens and the alkylene radicals at $C_3$-$C_5$ forming, with the adjacent carbon atoms, an aliphatic or aromatic cycle, including the p-methylphenyl, p-ethylphenyl, 2,4-dimethylphenyl, 3,4-dimethylphenyl, 2,4,5-trimethylphenyl and indolinyl radicals. Preferably, R represents an unsubstituted phenyl radical or a phenyl radical substituted by 1 to 3 radicals chosen from the group including the alkyl radicals at $C_1$-$C_4$, the halogens and the alkylene radicals at $C_3$-$C_5$ forming, with the adjacent carbon atoms, an aliphatic cycle.

It is possible to react the polyol with a mixture of aldehydes, which results in a polyol substituted by acetals having identical or different substituents (symmetric or asymmetric diacetals, respectively). The aldehyde advantageously reacts with the polyol to form acetals in positions 1:3 and 2:4.

The organogelator can be a monosubstituted polyol, preferably in position 1:3 or in position 2:4, disubstituted, preferably in position 1:3 and in position 2:4, and, as the case may be (m=1) trisubstituted in positions 1:3, 2:4 and 5:6.

According to a particularly advantageous alternative of the invention, the organogelator is chosen from the group constituted by 1,3:2,4-di-O-benzylidene-D-sorbitol, 1,3:2,4:5,6-tri-O-benzylidene-D-sorbitol, 2,4-mono-O-benzylidene-D-sorbitol, 1,3:2,4-di-O-benzylidene-D-xylitol and 2,4-mono-O-benzylidene-D-xylitol.

The 1,3:2,4-di-O-benzylidene-D-sorbitol is a compound with the following formula:

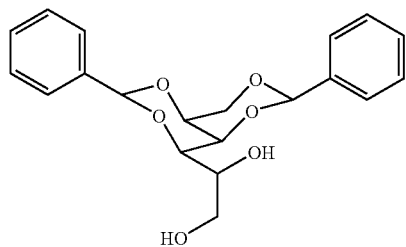

The particles according to the invention are oblong, and advantageously have a spindle or rod shape.

The technology for preparing microparticles by diffusion of solvents is well known and widely used in the preparation of polymer microspheres capable of including various active principles. In this technique, the polymer is dissolved in an organic solvent non-miscible with water. This organic phase is then emulsified in water advantageously containing a dispersant (PVA or Tween® 80, for example). Then, the solvent is evaporated in order to recover the microspheres. In the present invention, the organic phase constituted by the polymer dissolved in a solvent is replaced by an organogel obtained by dissolving an organogelator in a solvent non-miscible with water. Microparticles not having a microsphere shape, but constituted by fine fibers primarily associated in bundles, are then obtained.

The invention therefore also relates to a process for particle synthesis, characterized in that it includes the following series of steps:

a) dissolving the organogelator in a volatile organic solvent non-miscible with water S1;

b) pouring the mixture obtained from step a), under mechanical stirring, into an aqueous solution, which includes a surfactant or a polymer;

c) recovering and drying the particles obtained from step b).

The polymer is advantageously a water-soluble polymer.

The solvent S1 is advantageously chosen from the group constituted by chloroform, methylene chloride, dichloromethane, dichloroethane, aliphatic hydrocarbons, halogenated aliphatic hydrocarbons, aromatic hydrocarbons, halogenated aromatic hydrocarbons, ethers, ethyl acetate, ethyl formate and mixtures thereof. More advantageously, the solvent S1 is ethyl acetate.

The mixture obtained in step a) is called an organogel in the context of this invention. The particles according to the invention can be prepared from the organogel by a solvent evaporation process (first alternative), a solvent diffusion/evaporation process (second alternative) or by a shearing process (third alternative).

The particles according to the invention can also comprise an external layer including a coating agent, around the external surface of said external envelope enveloping the assembly constituted by said fibers. To do this, a coating agent soluble in the solvent S1 is advantageously used. In particular, the particles are coated with a polymer, which makes it possible in particular to stabilize the spindles or to modulate the refractive indices. The coating agent is advantageously added to the organogel in proportions ranging from 5% to 50% by weight, with respect to the weight of the organogelator, preferably 25% by weight, with respect to the weight of the organogelator. When the organogelator is DBS, the preferred coating agent is polymethyl methacrylate (PMMA).

According to a first alternative of the invention, the particles have a spindle shape with a length between 5 and 100 µm.

These particles can be obtained by a solvent evaporation process. In particular, the particles are obtained by a process of the invention including the following series of steps:

a) dissolving 0.1 to 10% by weight of the organogelator, with respect to the volume of the solvent S1, in the solvent S1;

b) i) pouring the mixture obtained from step a), under mechanical stirring, into an aqueous solution, which includes a surfactant or a polymer;

ii) stirring the mixture obtained in step b)i) until the solvent S1 is completely evaporated;

c) recovering and drying the spindle-shaped particles between 5 and 100 µm obtained from step b)ii).

The polymer is advantageously a water-soluble polymer.

The solvent S1 is advantageously chosen from the group defined above.

In step a), the mixture (solvent and organogelator) can be heated so as to facilitate and accelerate the dissolution of the organogelator in the solvent S1. In particular, the mixture can be heated to a temperature between 30 and 150° C., advantageously a temperature of around 75° C.

In step a), DBS is preferably used in the ethyl acetate, which DBS is used at a concentration of 4% by weight, with respect to the volume of ethyl acetate.

In the dispersion step b)i), the mixture obtained in step a) (organogelator: preferably DBS) is advantageously poured under mechanical stirring into an aqueous solution including:
- a surfactant, in particular Tween® 80, at a concentration of 0.1 to 1% by weight, preferably 0.5% by weight, with respect to the total weight, or
- a polymer, in particular a water-soluble polymer, in particular PVA hydrolyzed at 98 to 99%, with a Mw between 5000 and 100,000 g·mole$^{-1}$, preferably between 30,000 and 50,000 g·mole$^{-1}$, at a concentration of 0.1 to 5% by weight, and preferably 2% by weight, with respect to the total weight.

In stirring/evaporation step b)i), the mixture is advantageously stirred at a temperature of between 20° C. and 90° C., until complete evaporation of the solvent S1. In particular, when the organogelator substance is DBS and the solvent S1 is ethyl acetate, the mixture is advantageously stirred at a temperature of around 25° C.

In step c) of recovering particles/drying, the particles are advantageously recovered by centrifugation. They are then advantageously washed in water and dried by lyophilization.

The particles thus obtained have a spindle shape, and are advantageously microscopically iridescent, with a width of between 1 and 15 μm, a thickness of between 1 and 2 μm and a length of between 5 and 100 μm. These spindles are constituted by an alignment of organogelator molecules organized in strips with a width ranging from 50 to 100 nm. However, on the side, there may also be spindles from various debris constituted by longer fibers, which will settle when the lyophilized particles are redispersed in water.

These particles can also comprise an external layer including a coating agent, enveloping said fiber mass, around the external surface of said external envelope. In this case, the preparation process includes an additional coating step consisting of adding 5 to 50% by weight, and advantageously 25% by weight, with respect to the weight of the organogelator, of a coating agent (advantageously a polymer) soluble in the solvent S1. When the organogelator is DBS, the preferred coating agent is PMMA. Then, in step a), the organogel will be prepared with the organogelator (DBS) and one part of ethyl acetate, then the other part of the ethyl acetate, in which the coating agent (PMMA) is dissolved, will be added.

The invention also relates to spindle-shaped particles in the form of a mass constituted essentially by a plurality of fibers of an organogelator in xerogel form, wherein the fibers are essentially oriented in the same main direction defining the length of the particle, which is between 5 and 100 μm, and comprise an external envelope, including a polymer or a surfactant, enveloping said fiber mass, wherein said particles are capable of being obtained by a process including the following series of steps:
a) dissolving 0.1 to 10% by weight of the organogelator, with respect to the volume of the solvent S1, in a volatile organic solvent non-miscible with water S1;
b) i) pouring the mixture obtained from step a), under mechanical stirring, into an aqueous solution, which includes a surfactant or a polymer;
   ii) stirring the mixture obtained in step b)i) until the solvent S1 is completely evaporated;
c) recovering and drying the spindle-shaped particles between 5 and 100 μm obtained from step b)ii).

The characteristics of the process are the same as those described above, in the context of the first alternative of the invention. The organogelator is advantageously DBS and the solvent S1 is advantageously ethyl acetate. These particles can also be coated with an additional external layer, advantageously a polymer, in particular PMMA.

According to a second alternative of the invention, the particles are spindle shaped with a length of between 2 and 30 μm, and advantageously between 2 and 10 μm. These particles can be obtained by a solvent diffusion and evaporation process. In particular, the particles are obtained by a process of the invention including the following series of steps:
a) i) dissolving 0.1 to 50% by weight of the organogelator, with respect to the volume of solvents S0+S1, in a non-volatile organic solvent miscible with water S0;
   ii) adding solvent S1, in volume proportions S0/S1 ranging from 25/75 to 90/10;
b) i) pouring the mixture obtained from step a)ii), under mechanical stirring, into an aqueous solution, and a surfactant or a polymer is then dispersed in this mixture;
   ii) stirring the mixture obtained in step b)i) until the solvent S1 is completely evaporated;
c) recovering and drying the spindle-shaped particles with a length between 2 and 30 μm, and advantageously between 2 and 10 μm, obtained from step b)ii).

The polymer is advantageously a water-soluble polymer.

Solvent S1 is advantageously chosen from the group defined above. In particular, solvent S1 is ethyl acetate.

Solvent S0 is advantageously chosen from the group constituted by acetone, acetonitrile, ethanol, methanol, propanol-2, dioxane, dimethylformamide, dimethylsulfoxide, tetrahydrofurane and mixtures thereof. In particular, the solvent is DMSO.

In step a)i), the mixture (solvent and organogelator) can be heated so as to facilitate and accelerate the dissolution of the organogelator in solvent S0.

In step a) of preparing the organogel (or viscous liquid), advantageously, the organogelator is first dissolved in a non-volatile organic solvent miscible with water (S0), at a concentration of 0.1 to 50% by weight of organogelator/volume of solvents S0+S1, and preferably at a concentration of around 20% by weight of organogelator/volume of solvents S0+S1. The final volume is then completed with a volatile solvent non-miscible with water (S1 as defined above), in volume proportions of S0/S1 ranging from 25/75 to 90/10, and preferably in volume proportions of 50/50. In the dispersion step b)i), an emulsion is then formed and the solvent S0 diffuses quickly from these droplets, reducing their size.

Particularly advantageously, the organogelator is DBS, solvent S0 is DMSO and solvent S1 is ethyl acetate.

In the dispersion step b)i), an additive, which is a surfactant or a polymer, advantageously a water-soluble polymer, is added after introduction of the organogel into the aqueous solution. In particular, the additive is PVA or Tween® 80, in an amount so that eventually a solution with 2% PVA or 0.5% Tween® 80 is obtained.

In the stirring/evaporation step b)ii), the solvent S1 (advantageously ethyl acetate) remaining in the droplets evaporates progressively during the mechanical stirring. When the organogelator is DBS, solvent S0 is DMSO, and solvent S1 is ethyl acetate, this stirring is advantageously performed at a temperature of 25° C. The particles then form. They are advantageously recovered by centrifugation and washed in water, then dried by lyophilization (step c).

The particles thus obtained have a very small spindle shape with a width of between 0.4 and 1 micron, and a length of between 2 and 10 microns. These thin spindles are constituted by an alignment of substantially fused organogelator strips. The advantage of this second alternative is that there is not, next to the spindles, debris constituted by longer fibers that will settle when the lyophilized particles are redispersed in water (unlike in the first alternative).

These particles can also comprise an external layer including a coating agent, enveloping said fiber mass, around the external surface of said external envelope. In this case, the preparation process includes an additional coating step consisting of adding 5 to 50% by weight, and advantageously 25% by weight, with respect to the weight of the organogelator, of a coating agent (advantageously a polymer) soluble in the solvent S1. When the organogelator is DBS, the preferred coating agent is PMMA. Then, in step a), the organogel will be prepared with the organogelator (DBS) and one part of ethyl acetate, then the other part of the ethyl acetate, in which the coating agent (PMMA) is dissolved, will be added. The invention also relates to spindle-shaped particles in the form of a mass constituted essentially by a plurality of fibers of an organogelator in xerogel form, wherein the fibers are essentially oriented in the same main direction defining the length of the particle, which is between 2 and 30 µm, and advantageously between 2 and 10 µm, and comprise an external envelope, including a polymer or a surfactant, enveloping said fiber mass, in which said particles are capable of being obtained by a process including the following series of steps:
a) i) dissolving 0.1 to 50% by weight of the organogelator, with respect to the volume of solvents S0+S1, in a non-volatile organic solvent miscible with water S0;
   ii) adding solvent S1, in volume proportions S0/S1 ranging from 25/75 to 90/10;
b) i) pouring the mixture obtained from step a)ii), under mechanical stirring, into an aqueous solution, and a surfactant or a polymer is then dispersed in this mixture;
   ii) stirring the mixture obtained in step b)i) until the solvent S1 is completely evaporated;
c) recovering and drying the spindle-shaped particles with a length between 2 and 30 µm, and advantageously between 2 and 10 µm, obtained from step b)ii).

The characteristics of the process are the same as those described above, in the context of the first alternative of the invention. Particularly advantageously, the organogelator is DBS and solvent S0 is DMSO, and solvent S1 is ethyl acetate. These particles can also be coated, advantageously by a polymer, in particular PMMA.

According to a third alternative of the invention, the particles are rod shaped with a length of around 25 µm.

These particles can be obtained by a shearing process, in particular a shearing process that does not include a step of evaporating organic solvents from an aqueous emulsion, which emulsion is therefore suitable for industrial use. The particles are advantageously obtained by a process of the invention including the following series of steps:
a) dissolving 0.1 to 10% by weight of the organogelator, with respect to the volume of the solvent S1, in the solvent S1;
b) i) drying the mixture obtained from step a) at reduced pressure and recovering a xerogel powder;
   ii) shearing and dispersing the xerogel powder obtained in step b)i) in an aqueous solution, which includes a surfactant or a polymer;
c) recovering and drying the rod-shaped particles having an average length of around 25 µm obtained from step b)ii).

Solvent S1 is advantageously chosen from the group defined above. In particular, S is ethyl acetate. The polymer is advantageously a water-soluble polymer.

In step a) the mixture (solvent and organogelator) can be heated so as to facilitate and accelerate the dissolution of the organogelator in the solvent S1. In particular, the mixture can be heated to a temperature between 30 and 150° C., advantageously a temperature of around 75° C. when S1 is ethyl acetate and the organogelator is DBS. In step a), DBS is preferably used in ethyl acetate, which DBS is used at a concentration of 4% by weight, with respect to the volume of ethyl acetate.

The mixture obtained in step a) (organogel) is then dried at reduced pressure so as to completely remove solvent S1 (ethyl acetate) and obtain the organogel in xerogel powder form (step b)i)). This xerogel powder is constituted by very long fibers of the organogelator, which are sheared and mechanically dispersed in an aqueous solution that advantageously contains a dispersant, which is advantageously Tween® 80 (step b)ii)). The breakage of the fibers, as well as their dispersion, can be obtained by very strong stirring with powerful "ultraturax"-type stirrers, or by sonication. Preferably, it will be decided to shear and disperse the organogel by sonication of the aqueous solution also containing the dispersant. Iridescent rods with an average length of 25 µm are then obtained.

The invention also relates to rod-shaped particles in the form of a mass, essentially constituted by xerogel fibers of an organogelator substance, wherein the fibers are essentially oriented according to the same main direction defining the length of the particle, which is around 25 µm, and comprise an external envelope, including a polymer or a surfactant, enveloping said fiber mass, in which said particles are capable of being obtained by a process including the following steps:
a) dissolving 0.1 to 10% by weight of the organogelator, with respect to the volume of the solvent S1, in a volatile organic solvent S1;
b) i) drying the mixture obtained from step a) at reduced pressure and recovering a xerogel powder;
   ii) shearing and dispersing the xerogel powder obtained in step b)i) in an aqueous solution, which includes a surfactant or a polymer;
c) recovering and drying the rod-shaped particles having an average length of around 25 µm obtained from step b)ii).

The characteristics of the process are the same as those described above, in the context of the third alternative of the invention. Particularly advantageously, the organogelator is DBS and the solvent S1 is ethyl acetate.

The particles according to the invention (as described above, in particular particles according to the first, second or third alternative) advantageously have a total light transmittance greater than 0.80, with a diffuse transmittance greater than the specular transmittance.

When the light hits a material, it can be transmitted or reflected each time in a diffuse (multidirectional) or specular (monodirectional) manner, and absorbed. A material that transmits light completely has a total transmittance of 1. Thus, if the total transmittance is greater than 0.80, 80% of the light that reaches the particles is transmitted. The particles are therefore transparent.

The particles advantageously have a total transmittance greater than 0.85, more advantageously greater than 0.90, and even more advantageously greater than 97% (transparency). The diffuse transmittance is greater than the specular transmittance, thus more than half of the light transmitted is done so diffusely. Advantageously, at least 90% of the light transmitted is diffused. The particles also have a low total reflectance. The particles advantageously have a diffuse reflectance greater than the specular reflectance. Thus, the light reflected is primarily done so diffusely.

The particles advantageously have a refractive index greater than 1.45. The particles are microscopically iridescent. It is assumed that each fiber constituting the oblong particle diffuses light. In the case of xerogel fibers of organogelator derived from carbohydrates or polyols, the difference in the refractive index between the polyol core (advantageously sorbitol or xylitol) and the sheath (radical R), advantageously aromatic, can lead to the formation of interferences.

These particles have the property of diffusing light. In addition, these particles have the following optical characteristics:

high total light transmission (transparency), which enables light to pass through the particles and be reflected on the surface to which the particles are applied (skin), thus preserving the natural hue of the surface (skin);

a large part of the component diffuses the transmission so as to enable the light to be reflected on the surface (skin) at a plurality of points, thereby hiding imperfections on the surface (skin);

low total reflection so as to prevent the projection of the color of the particle;

a large part of the component diffuses the reflection so as to minimize gloss.

These particles therefore have a soft-focus effect. The capacity of a particle to diffuse light, and therefore to have a soft-focus effect, can also be dependent on the difference between its refractive index and that of the medium. For example, PMMA microspheres used for this purpose have a refractive index of 1.49, whereas the media normally used in cosmetics have an index between 1.33 and 1.6. When the difference is too small, there is no diffusion and the particles are transparent. By contrast, when the difference is too great, the reflectivity increases, which gives an opaque and unnatural appearance.

In addition, the spindles or rods could also serve as an optical guide in the direction of the fibers. If the refractive index of the organogelator is greater than that of the medium, an analogy with the optical fibers can be made. The light, guided by the spindle, could then illuminate interior of the imperfections of the substrate (skin wrinkles), which thus appear less dark. When the oblong particles are coated with a material with a refractive index lower than that of the organogelator, this effect is accentuated.

Moreover, the spindles or rods have the advantage of having a larger area of contact with the surface (skin) than in the case of microspheres.

The invention also relates to active particles constituted by particles as defined above on which dermocosmetically active principle is immobilized. In a non-limiting manner, this dermocosmetically active principle may be a dye, a pigment, liquid crystals, a vitamin, an active principle with a therapeutic action, a sunscreen or a combination of these various active principles.

The active principles are immobilized without substantially modifying the size of the particles and without modifying their optical properties.

The invention also relates to a dermocosmetic composition including particles as defined above or active particles as defined above and a dermocosmetically acceptable carrier. In particular, the invention relates to a cosmetic composition and a pharmaceutical composition (dermatological).

The particles according to the invention and the active particles according to the invention are advantageously spindle- or rod-shaped, which makes it possible to increase their surface of contact with the skin (by comparison with a sphere). The range of particle sizes obtained is also suitable for the depth of the wrinkles (around 80 µm) and lines (up to 40 µm).

The particles according to the invention also have the advantage of not adversely affecting the skin pH. Moreover, the particles preserve their morphology for many weeks after dispersion.

The invention finally relates to a cosmetic treatment method for masking wrinkles, lines and other skin imperfections, and/or for obtaining a uniform hue, characterized in that it consists of applying a composition as defined above on the skin.

The particles according to the invention can be used in foundations in order to enhance the skin's brightness and mask wrinkles, while preserving the natural appearance of the skin. The particles according to the invention have the property of diffusing light, which produces a natural satin effect, by contrast with opaque particles (such as $TiO_2$), which whiten the skin and give it a matte appearance.

The compositions according to the invention can also be used at the same time to mask an imperfection of the skin and treat the origin of this imperfection. Thus, they can be used to obtain a uniform appearance of the skin, to mask redness, spots, in particular pigment spots, or pimples, while containing an active principle for treating acne, vitiligo, hyperpigmentation, erythema, allergies, dermatosis, dermatitis, eczema or autoimmune diseases (psoriasis), in which the active principle is immobilized on the particles according to the invention.

According to an advantageous embodiment of the invention, the active principle immobilized on the particles according to the invention is a sunscreen, in particular a liquid sunscreen such as Eusolex® 2292 (ethylhexyl methoxycinnamate, UVB filter) or Eusolex® 9020 (butyl methoxydibenzoylmethane, UVA filter). This UVA filter is advantageously dissolved in the UVB filter. The properties of light diffusion by the particles would enable the spindles not containing sunscreen to direct the UV radiation toward spindles containing it. The protection would then be increased even in the presence of a reduced amount of sunscreen.

The oblong iridescent particles according to the invention, in particular the oblong iridescent DBS particles, have the following properties:

semi-transparent particles with soft-focus effect on a large surface rotating polarization of light for a skin application, form suitable for masking wrinkles and lines coverage area greater than with a sphere adjustable spindle or rod size biocompatible particles chemical stability (acid medium)

easy preparation of spindles

DBS inexpensive and already approved for cosmetic uses possibility of having optical guidance of light possibility of easily staining particles chemical modulation of aromatic substituents (UV Filter, Refractive Index, Coloring)

possibility of modulating the refractive indices of the spindles (polymer coating).

The following examples are non-limiting illustrations of various processes for preparing particles according to the invention.

EXAMPLE 1

Process According to the First Alternative

Preparation of the organogel: the gel (or viscous liquid) is prepared from a 4% mass/volume DBS solution, i.e. 0.2 g in 5 ml of anhydrous ethyl acetate. To totally dissolve the DBS in the solvent, the mixture is brought to reflux (75° C.) before being cooled at room temperature so as to form a viscous liquid.

Dispersion: the viscous liquid is poured, at 25° C., under mechanical stirring at 1430 revolutions/minute (4-blade stirrer) in 100 ml of a Tween® 80 solution at 0.5% by weight in water.

Stirring/evaporation: the solvent progressively evaporates during the mechanical stirring at 1430 revolutions/minute for a period of 3 hours 30 minutes at 25° C.

Recovery of particles: the particles are recovered by centrifugation for 20 minutes at 8700 revolutions/minute. They are then washed 5 times in water.

Drying by lyophilization: the particles are dried by lyophilization for 24 hours. The particle yield is 54%. The particles are then characterized by optical and electron microscopy. The morphology and size distribution are determined by imaging techniques. Polydisperse spindle-shaped particles are obtained with an average size of 19 μm in length and 1 μm in width.

EXAMPLE 2

Process According to the Second Alternative

Preparation of the organogel: the gel or viscous liquid is prepared by dissolving, at room temperature, 1 g of DBS in 2.5 ml of anhydrous DMSO, then by adding 2.5 ml of ethyl acetate for a final volume of 5 ml and a DBS concentration of 20% mass/volume.

Dispersion and diffusion: the viscous liquid is poured drop-by-drop at 25° C. under mechanical stirring at 1430 revolutions/minute in 75 ml of water.

Addition of the dispersant/stabilization: after 3 minutes of stirring, 25 ml of a Tween® 80 solution is added so as to obtain a final mass concentration of 0.5%.

Stirring and evaporation of the solvent: the ethyl acetate progressively evaporates during the mechanical stirring for a period of 3 hours.

Recovery of particles: the particles are recovered by centrifugation for 20 minutes at 8700 revolutions/minute. They are then washed 5 times in water.

Drying by lyophilization: the particles are dried by lyophilization for 24 hours. The particle yield is 84%. The particles are then characterized by optical and electron microscopy. The morphology and size distribution are determined by imaging techniques. Spindle-shaped particles less polydisperse than in example 1 are obtained with an average size of 5 μm in length and 0.4 μm in width.

EXAMPLE 3

Obtaining Coated Particles

The protocol of example 1 is used, but with the addition of 5% by weight of PMMA (Mw=15000) with respect to the DBS. As in example 1, polydisperse spindle-shaped particles are obtained, with an average size of 19 μm in length and 1 μm in width.

EXAMPLE 4

Process According to the Third Alternative

Preparation of the organogel: the gel (or viscous liquid) is prepared from a 4% mass/volume DBS solution, i.e. 0.2 g in 5 ml of anhydrous ethyl acetate. To totally dissolve the DBS in the solvent, the mixture is brought to reflux (75° C.) before being cooled at room temperature so as to form a viscous liquid.

Evaporation of the solvent: the ethyl acetate is evaporated with the rotary evaporator (40° C./120 mbars) for 1 hour. The solvent can be recycled for future use.

Organogel suspension: The organogel (0.198 g) obtained is added to 20 ml of an aqueous solution containing 0.1 g of Tween® 80 (0.5% mass/volume).

Mechanical shearing and dispersion: The mixture is mechanically sheared using an ultrasound probe (20 kHz, 600 W), per interval (1×5' and 2×10') for 25 minutes.

Recovery of particles: the particles are recovered by filtration on filter paper and are washed 5 times in water. The particles are then dried in a vacuum dryer at 60° C. for 24 hours. The mass yield in particles is 95%.

The particles are characterized by optical microscopy. The morphology and particle size distribution are determined by image analysis. Iridescent rod-shaped particles are obtained with an average size of 25 μm in length and 4 μm in width.

EXAMPLE 5

Encapsulation of a Sunscreen

The protocol of example 1 is used, but by dissolving 50% by weight of Eusolex 2292 (maximum absorption: 310 nm) with respect to the DBS, in the ethyl acetate used to prepare the organogel.

As in example 1, polydisperse spindle-shaped particles are obtained, with an average size of 19 μm in length and 1 μm in width. These particles contain on average 8.4% by weight Eusolex 2292 while preserving the optical properties of the particles obtained according to the process of example 1.

The cosmetic formulations are made primarily in an aqueous medium. It is therefore important to know whether the Eusolex 2292 remains in the microparticles in a medium with a similar composition. These microparticles were therefore dispersed in water with a concentration of 1 mg/ml. After 20 days of magnetic stirring, no Eusolex 2292 was released.

The microparticles developed by evaporation of solvent therefore have the advantage of immobilizing the Eusolex 2292, which preserves its properties of absorption in the UVB and of not releasing it in a medium similar to that used in the cosmetic formulations, while preserving their microscopic iridescence.

EXAMPLE 6

Encapsulation of a Pharmaceutically Active Principle

The protocol of example 2 is used, but by dissolving 0.8% by weight progesterone, with respect to the DBS, in the ethyl acetate used to prepare the organogel.

As in example 2, spindle-shaped particles are obtained, with an average size of 5 μm in length and 0.48 μm in width. These particles contain on average 0.48% by weight progesterone.

EXAMPLE 7

Optical Properties

The optical properties of the particles obtained by the solvent evaporation technique (first alternative) were measured on a visible spectrometer equipped with an integration sphere. The light that hits a sample can be absorbed, reflected of transmitted, with the reflected light and the transmitted light both having a specular component and a diffuse component.

The total of the light reflected and transmitted by the iridescent particles of the invention is high, and all of this light is diffused. The percentage of light transmitted is very high (transparency), at around 97%.

These properties correspond to the optical features that particles must have in order to have a good soft-focus effect.

The optical measurements performed on particles obtained by the solvent diffusion/evaporation technique showed similar results.

The invention claimed is:

1. A process for synthesizing oblong particles in the form of a mass constituted by a plurality of fibers of an organogelator selected from the group consisting of 1,3:2,4-di-O-benzylidene-D-sorbitol, 1,3:2,4:5,6-tri-O-benzylidene-D-sorbitol, 2,4-mono-O-benzylidene-D-sorbitol, 1,3:2,4-di-O-benzylidene-D-xylitol, and 2,4-mono-O-benzylidene-D-xylitol in xerogel form, in which the fibers are oriented according to the same main direction defining the length of the particle, which is between 2 and 100 µm, and comprise an external envelope, including a polymer or a surfactant, enveloping said fiber mass, wherein said particles have a total light transmittance greater than 0.80, with a diffuse transmittance greater than the specular transmittance, said process comprising the following series of steps:
   a) dissolving the organogelator in a volatile organic solvent non-miscible with water S1;
   b) pouring the mixture obtained from step a), under mechanical stirring, into an aqueous solution, which includes a surfactant or a polymer; and
   c) recovering and drying the particles obtained from step b).

2. Process according to claim 1, wherein it includes the following series of steps:
   a) dissolving 0.1 to 10% by weight of the organogelator, with respect to the volume of the solvent S1, in the solvent S1;
   b) i) pouring the mixture thus obtained, under mechanical stirring, into an aqueous solution, which includes a surfactant or a polymer;
   b) ii) stirring the mixture obtained in step b)i) until the solvent S1 is completely evaporated; and
   c) recovering and drying the spindle-shaped particles between 5 and 100 µm obtained from step b)ii).

3. A process for synthesizing oblong particles in the form of a mass constituted by a plurality of fibers of an organogelator selected from the group consisting of 1,3:2,4-di-O-benzylidene-D-sorbitol, 1,3:2,4:5,6-tri-O-benzylidene-D-sorbitol, 2,4-mono-O-benzylidene-D-sorbitol, 1,3:2,4-di-O-benzylidene-D-xylitol, and 2,4-mono-O-benzylidene-D-xylitol in xerogel form, in which the fibers are oriented according to the same main direction defining the length of the particle, which is between 2 and 100 µm, and comprise an external envelope, including a polymer or a surfactant, enveloping said fiber mass, said process comprising the following series of steps:
   a) i) dissolving 0.1 to 50% by weight of the organogelator, with respect to the volume of solvents S0+S1, in a non-volatile organic solvent miscible with water S0;
   a) ii) adding solvent S1, in volume proportions S0/S1 ranging from 25/75 to 90/10;
   b) i) pouring the mixture obtained from step a)ii), under mechanical stirring, into an aqueous solution, and a surfactant or a polymer is then dispersed in this mixture;
   b) ii) stirring the mixture obtained in step b)i) until the solvent S1 is completely evaporated; and
   c) recovering and drying and freezing at reduced temperature the spindle-shaped particles with a length between 2 and 30 µm, obtained from step b)ii).

4. Process according to claim 1, wherein it includes an additional coating step consisting of adding 5 to 50% by weight, with respect to the weight of the organogelator, of a coating agent, which is a polymer, soluble in the solvent S1.

5. A process for synthesizing oblong particles in the form of a mass constituted by a plurality of fibers of an organogelator selected from the group consisting of 1,3:2,4-di-O-benzylidene-D-sorbitol, 1,3:2,4:5,6-tri-O-benzylidene-D-sorbitol, 2,4-mono-O-benzylidene-D-sorbitol, 1,3:2,4-di-O-benzylidene-D-xylitol, and 2,4-mono-O-benzylidene-D-xylitol in xerogel form, in which the fibers are oriented according to the same main direction defining the length of the particle, which is between 2 and 100 µm, and comprise an external envelope, including a polymer or a surfactant, enveloping said fiber mass, said process comprising the following series of steps:
   a) dissolving 0.1 to 10% by weight of the organogelator, with respect to the volume of the solvent S1, in the solvent S1;
   b) i) drying the mixture thus obtained at reduced pressure and recovering a xerogel powder;
   b) ii) shearing and dispersing the xerogel powder obtained in step b)i) in an aqueous solution, which includes a surfactant or a polymer; and
   c) recovering and drying the rod-shaped particles having an average length of around 25 µm obtained from step b)ii).

6. Process according to claim 1, wherein the solvent S1 is chosen from the group constituted by chloroform, methylene chloride, dichloromethane, dichloroethane, aliphatic hydrocarbons, halogenated aliphatic hydrocarbons, aromatic hydrocarbons, halogenated aromatic hydrocarbons, ethers, ethyl acetate, ethyl formate and mixtures thereof.

7. Process according to claim 3, wherein the solvent S0 is chosen from the group constituted by acetone, acetonitrile, ethanol, methanol, propanol-2, dioxane, dimethylformamide, dimethylsulfoxide, tetrahydrofurane and mixtures thereof.

8. Cosmetic treatment method for masking wrinkles, lines and other skin imperfections, and/or for obtaining a uniform hue, characterized in that it consists of applying to the skin of a person in need thereof a composition comprising
   oblong particles in the form of a mass constituted by a plurality of fibers of an organogelator selected from the group consisting of 1,3:2,4-di-O-benzylidene-D-sorbitol, 1,3:2,4:5,6-tri-O-benzylidene-D-sorbitol, 2,4-mono-O-benzylidene-D-sorbitol, 1,3:2,4-di-O-benzylidene-D-xylitol, and 2,4-mono-O-benzylidene-D-xylitol in xerogel form, in which the fibers are oriented according to the same main direction defining the length of the particle, which is between 2 and 100 µm, and comprise an external envelope, including a polymer or a surfactant, enveloping said fiber mass, wherein said particles have a total light transmittance greater than 0.80, with a diffuse transmittance greater than the specular transmittance, and
   a cosmetically acceptable carrier.

9. The process according to claim 6, wherein the solvent S1 is ethyl acetate.

10. The process according to claim 7, wherein the solvent S0 is DMSO.

* * * * *